United States Patent [19]

Stuart

[11] 4,372,405

[45] Feb. 8, 1983

[54] WEIGHT, VOLUME OR DENSITY MEASURING SYSTEM

[76] Inventor: James M. Stuart, 2074 Yellow Springs Rd., Malvern, Pa. 19355

[21] Appl. No.: 233,525

[22] Filed: Feb. 11, 1981

[51] Int. Cl.³ .................. G01G 19/04; G01G 5/02; G01G 3/14; G01N 9/00
[52] U.S. Cl. .................. 177/25; 177/207; 177/210 C; 73/437
[58] Field of Search ............ 177/25, 165, 207, 210 C; 73/433, 437

[56] References Cited

U.S. PATENT DOCUMENTS

| | | | |
|---|---|---|---|
| 2,689,082 | 9/1954 | Kolisch | 177/25 X |
| 3,117,454 | 1/1964 | Pierce | 177/207 X |
| 3,388,585 | 6/1968 | Hargens | |
| 3,661,015 | 5/1972 | Paul | 73/437 |
| 3,991,619 | 11/1976 | Appleford et al. | 73/437 |
| 4,320,658 | 3/1982 | Hilton et al. | 177/207 X |

FOREIGN PATENT DOCUMENTS

777941 7/1957 United Kingdom ............ 177/210 C

*Primary Examiner*—George H. Miller, Jr.
*Attorney, Agent, or Firm*—Caesar, Rivise, Bernstein & Cohen, Ltd.

[57] ABSTRACT

Apparatus for determining the weight, density or volume of a solid body and the weight and density of a liquid. The apparatus comprises a capacitive transducer means and compensating means therefor, as well as electronic circuitry comprising computing means including memory means, calculating means, control means and digital display means. Methods of determining the weight, density or volume of solids and the weight and density of liquids are also disclosed.

17 Claims, 9 Drawing Figures

WEIGHT, VOLUME OR DENSITY MEASURING SYSTEM

This invention relates generally to measuring apparatus and more particularly to apparatus for directly measuring weight or density of a liquid or solid.

Various electronic scales are available commercially for providing a digital display of the weight of a body placed on the scale pan. Recently developed scales have made use of integrated circuits and microcomputer controls for effecting various scale operations such as weighing, counting, altering resolution, converting units, etc.

Heretofore, in order to determine the density of a liquid or solid using prior art scales, it is necessary to manually calculate the density by dividing the volume of the material to be determined into the weight as sensed by the scale. While the patent literature discloses various scales including computing means, such as U.S. Pat. Nos. 4,055,748 and 4,055,753, such devices do not produce a direct calculation of density of a solid or liquid. In U.S. Pat. No. 3,747,416, while there is disclosed apparatus for determining density of a solid, it does not appear suitable for effecting conventional weighing operations.

Accordingly, it is a general object of the instant invention to provide a scale which overcomes the disadvantages of the prior art.

It is a further object of the instant invention to provide apparatus for determining either the weight or density of a solid or liquid placed on the apparatus without requiring manual calculation.

It is a further object of the instant invention to provide a scale which is formed of solid state components for automatically determining the weight or density of a liquid or solid and for determining the weight, density or volume of a solid and for displaying the measured reading.

It is a further object of the instant invention to provide a scale using capacitive transducer means for effecting the operation.

It is a further object of the instant invention to provide apparatus for either weighing or determining the density of a solid or liquid and for providing a display based thereon, which apparatus includes capacitive transducer means and means for compensating for temperature variations and variations in the dielectric constant of the ambient atmosphere.

These and other objects of the instant invention are achieved by providing scale apparatus comprising platform means arranged to be displaced upon receipt of some material thereon, support means for said platform means, variable capacitance means coupled to said platform means for providing a first electrical signal indicative of the amount of movement of said platform means, fixed capacitance means for providing a second electrical signal dependent upon the dielectric constant of the ambient atmosphere, temperature responsive means for providing a third electrical signal dependent upon ambient temperature and means for receiving said first, second and third signals for providing a fourth signal indicative of the weight of said material.

The apparatus is arranged for automatically determining the weight, volume or density of an unknown solid or the weight or density of an unknown liquid placed upon said platform means and comprises computing means including memory means, calculating means and control means. The memory means is coupled to the calculating means and the control means for automatically calculating the density of said material, and the display means displays the calculated density.

Other objects and many of the attendant advantages of the instant invention will be readily appreciated as the same becomes understood by reference to the following detailed description when considered in connection with the accompanying drawing wherein.

Figure 1:
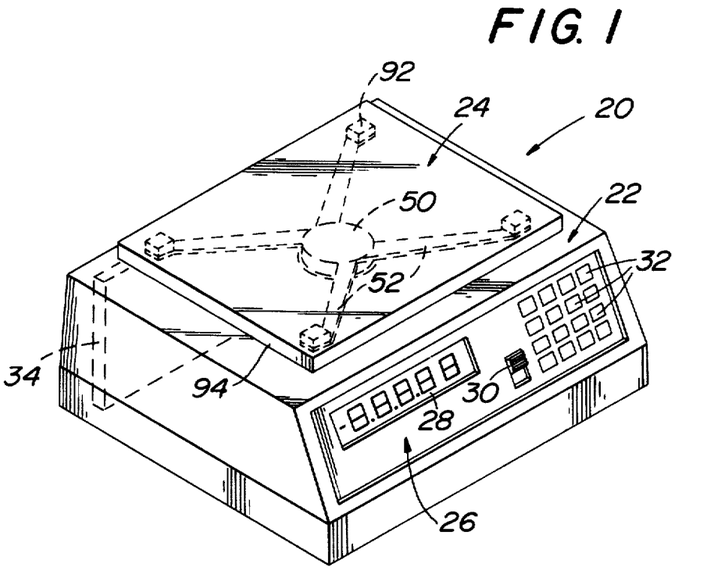
FIG. 1 is a perspective view of the apparatus constructed in accordance with the instant invention.

Referring now to the various figures of the drawing wherein like reference characters refer to like parts there is shown generally at 20 in FIG. 1 a scale/density measuring apparatus constructed in accordance with the instant invention. The scale/density measuring apparatus 20 is a self-contained, solid state, device suitable for determining either the weight or density of unknown liquids or solids or of the volume of unknown solids and for providing a digital reading of said weight, density or volume. The apparatus basically comprises a housing or casing 22 including a displacable platform or pan 24 arranged for receipt of either the liquid or solid to be measured. A control display panel 26 is on the front of the housing and includes a digital display 28, such as formed by a plurality of liquid crystal or light emitting diode elements, an on/off switch 30 and an array of depressable buttons or keys 32. The keys serve as the mechanism for providing instructions to the apparatus 20 to carry out a particular measuring or calculating routine, as will be set forth in detail later. Among the keys 32 are a "Weigh" key a "Calculate Density", a "Calculate Tare" key, an "Optional Liquid" key, a "Standard Liquid" key and various other keys, whose identity need not be set forth herein.

In the interior of the casing there is located displacement responsive transducer means, and an electrical system including microprocessor means, memory means, including random access memory means and read only memory means, and control means for effecting the weighing or density determination action. The details of the electrical system is shown in the functional block diagram of FIG. 7 and is formed of various integrated circuits, whose identity and interconnection will be discussed in detail later, and which are mounted on a printed circuit board 34, shown by the phantom line in FIG. 1, and mounted within the housing 22.

The apparatus 20 can be utilized as a conventional scale, that is, to determine the weight of a solid or liquid placed on the pan 24. In that regard, the electrical circuitry of the apparatus 20 is arranged so that in normal operation the apparatus is in a "Weigh" mode to perform as a scale. In the "Weigh" mode, the scale provides a display of the weight of the object placed on its pan. The circuitry is arranged to periodically, e.g., approximately once each second, take a new weight reading so that the display is automatically updated. In the event that the apparatus had been in a density determination mode, it is necessary to depress the "Weigh" key to initiate weighing operation.

In a weighing operation, the body to be weighed is placed on the pan, whereupon the displacement of the pan, caused by the mass of the body, is sensed by the displacement responsive transducer means, to provide a signal which is acted upon by the electrical circuitry to provide a digital reading the weight of the liquid or solid.

One of the important aspects of the instant invention is its ability to directly calculate the density of an unknown liquid or solid and to display the calculated density on the display means.

The liquid density determination process carried out by the apparatus 20 basically comprises placing an unknown liquid within a container on the pan of the apparatus to weigh the combination. The apparatus is then "tared" by the depression of a "Tare" key to store the tare weight in the system's random access memory and to subtract the tare weight from the measured weight, whereupon the apparatus displays the net weight of "Zero". A reference body of known volume is then suspended by suspension means within the liquid. The buoyance force, which is the weight of the displaced liquid, is automatically measured by the apparatus upon the depression of the "Density" and "1" keys and is the weight sensed by the apparatus 20 since it had just been "tared". The apparatus then takes weight of the displaced liquid and automatically divides it by the value of the volume of the known body which had been previously stored in memory to calculate the density of the liquid. The calculated density is then displayed on the digital display. The calculated density of the liquid can be made available for use in future density measurements by the depression of a "Density Store" key, whereupon the calculated density is stored in the system's random access memory. In order to return the apparatus to the "Weigh" mode, it is necessary to depress the "Weigh" key.

Figure 6:
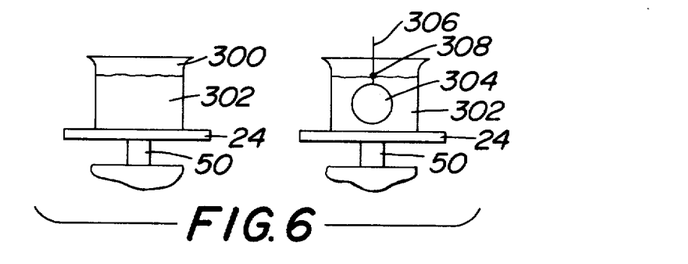
FIG. 6 is a schematic view showing various steps of the liquid density measuring routine or process performed by the apparatus of the instant invention.
Figure 8:
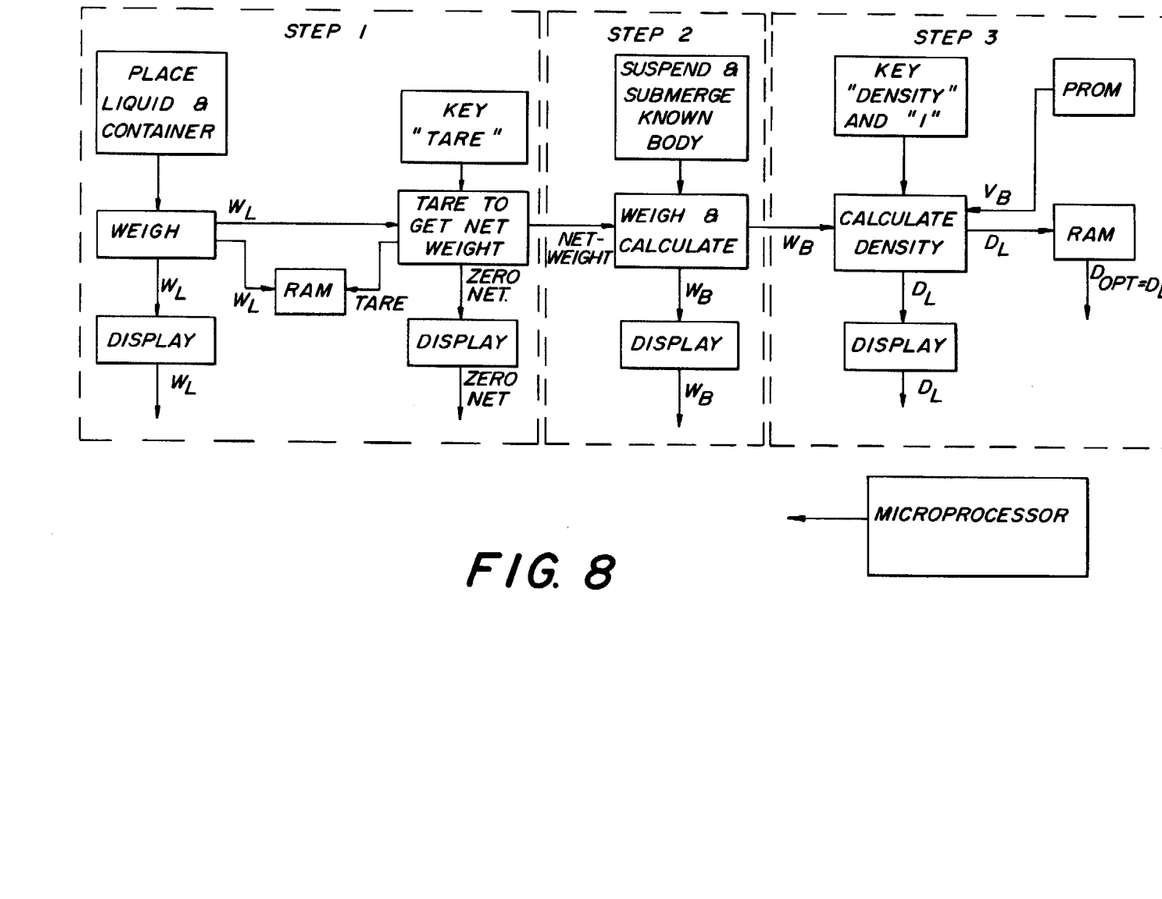
FIG. 8 is a block diagram showing the steps of the method of determining density as performed by the apparatus of the instant invention.

Referring now to FIGS. 6 and 8, the detailed operation of the system when determining the density of an unknown liquid will now be described. To that end, as can be seen in FIG. 8, the determination of the density of the unknown liquid is accomplished in three steps, each of which is shown schematically by the material bounded by the broken lines in FIG. 8.

In the first step, a container 300, such as a beaker, containing the unknown liquid 302 is placed on the apparatus platform 24, whereupon the apparatus weighs the beaker and liquid. The combined weight $W_L$ is displayed on the display means. The scale is then "tared" by depressing the "Tare" key. This action causes the weight of the liquid and container to be stored in the random access memory, and to be subtracted from itself, whereupon the display shows the net weight, i.e., zero. In Step 2, a known body 304 is suspended from a thin wire 306 held in one's hand or by means (not shown). The suspended body is submerged fully within the liquid 302, making sure that the body does not make contact with either the sides or bottom of the container. Since the body is suspended by the wire, the buoyancy force $W_B$ produced on the body and which is equal to the weight of the liquid displaced by the body is displayed on the display means 28. Since the scale had previously been "tared", only the weight of the liquid displaced (buoyance force) $W_B$ is calculated and displayed. The "Density" and "1" keys 32 are then depressed to initiate Step 3, whereupon the volume $V_B$ of the body 304 which had been stored in a programmable read only memory (PROM), to be described later, is recalled and divided into the weight of the liquid displaced to determine the density $D_L$ of the liquid. The density $D_L$ of the liquid is displayed on display means and, if the "Store Density" key is depressed, is also stored within the random access memory. The storage of the value of the unknown liquid's density will then be available for use as a "optional liquid", $D_{OPT}$, in a solid density measuring routine to be described later.

It must be pointed out at this juncture that the wire 306 for suspending the known body in the liquid necessarily displaces some liquid itself. Accordingly, to compensate for the amount of liquid displaced by the immersed suspending wire, the wire preferably includes a mark 308 thereon. The mark serves as a submersion reference point, with the volume of the wire below that point being known and stored in a read only memory. Accordingly, when the body is suspended in the liquid to the depth wherein the suspension mark is at the liquid surface, the submerged wire is equal to the volume which had been stored in the read only memory and is automatically added to the volume of the known body before being divided into the buoyance force reading. Thus, the system 20 compensates for the portion of the suspension wire within the liquid, thereby insuring accuracy of measurement.

The determination of the density of a solid can be accomplished by the apparatus 20 in various ways. The following description is a first type of routine and basically comprises placing an unknown solid sample on the scale pan to determine its weight. The "Weight Store" key is then depressed whereupon the measured weight of the unknown sample $W_S$ is stored within the random access memory. The sample is then removed from the pan and a reference liquid in a container is placed on the pan to effect the weighing of the liquid and container. The apparatus is then "tared" by depressing the "Tare" key, whereupon the system stores the weight of the reference liquid and container in the random access memory and subtracts the "Tare" weight from the weight on the pan. Thus, the apparatus displays a net weight of zero. The unknown solid sample is then suspended by suspension means within the reference liquid on the apparatus pan up until the reference mark on the suspension means, as described heretofore. The buoyance force, which is the weight $W_B$ of the displaced liquid, is automatically determined by the apparatus since the apparatus had previously been "tared". The density of the reference liquid is retrieved from memory by the depression of the "Density" and "2" keys and that density value is divided into the buoyance force $W_B$ previously determined to calculate the volume of the unknown solid sample plus the immersed portion of the suspension means. The volume of the immersed portion of the suspension means, which is stored in the read only memory, is recalled and subtracted from the calculated volume to yield the net volume, i.e., the volume of the sample, per se. The calculated volume of the unknown sample is automatically displayed. If the density of the solid is desired, the "Density" and "2" keys are depressed again, whereupon the sample volume heretofore calculated is divided into the weight of the unknown solid (which had been stored in the memory) to calculate the density of the unknown solid. The calculated density is automatically displayed by the display means. The apparatus 20 is restored to the "Weigh" mode of operation by the depression of the "Weigh" key.

An alternative or second type of routine for determining the density of the unknown solid requires a modification of the apparatus 20. First, the sample of the unknown solid is placed on the pan, whereupon the sample is weighed. The "Weight Store" key is then depressed to store the weight in the random access memory. The pan is then removed and a suspension assembly (not shown) is secured to the means which had supported the pan. The unknown sample is suspended by the suspension means in the air, and the "Tare" key is depressed. The suspension means has a mark on it serving as a submersion reference point like described heretofore, and the volume of the suspension means up to the submersion mark is stored in the read only memory. Using the mark, the sample is submerged in a liquid whose density had been previously stored in memory, whereupon the buoyancy force is displayed. The "Density" and "2" keys are then depressed, whereupon the liquid density (standard or optional, depending on whether an optional density has been stored in memory) is recalled from memory and divided into the buoyancy force. The result of this calculation is the volume of the sample plus the immersed portion of the suspension means. The volume of immersed portion of the suspension means, which is stored in the read only memory is recalled and subtracted from the calculated volume to yield the net volume, i.e., the volume of the sample, per se. This volume is automatically displayed. The "Density" and "2" keys are depressed again, whereupon the sample weight, previously stored in the random access memory is divided by the net sample volume to yield the density of the sample, which is automatically displayed.

Figure 5:
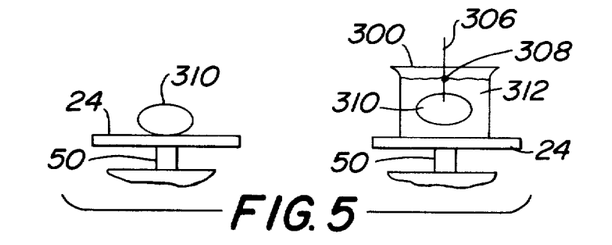
FIG. 5 is a schematic view showing various steps in the solid density measuring routine or process performed by the apparatus of the instant invention.
Figure 9:
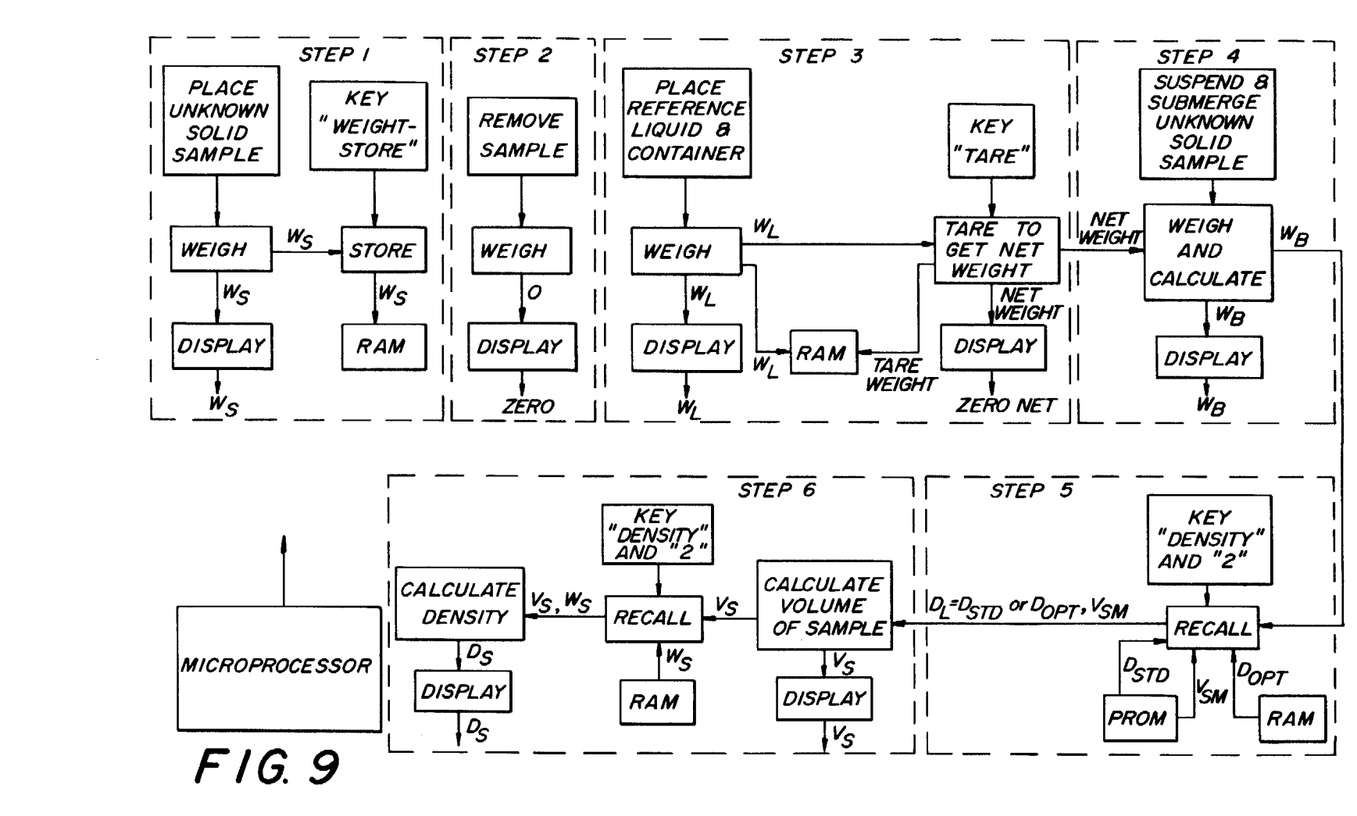
FIG. 9 is a block diagram showing steps for determining the density of a solid as performed by the apparatus of the instant invention.

The detailed operation of the first solid density determination routine will best be understood by reference to FIGS. 5 and 9. In this regard, the routine used to determine the density as shown in FIG. 9 consists of six steps, each of which is schematically shown by a respective broken-line box therein. To that end, in Step 1 the unknown solid sample or body 310 is weighed by placing it on the pan 24 of the apparatus, whereupon the sample is automatically weighed and a signal $W_S$, indicative of the weight of the sample, is provided to the display means 28 to display the measured weight. The "Weight Store" key is then depressed to store the signal $W_S$ in the random access memory for later use. Step 2 of the routine comprises removing the sample 310 from the pan, whereupon the display now reads "0". Step 3 consists of placing a known or reference liquid 312 in a container 300 on the apparatus pan. The liquid 312 may be a standard liquid, such as water, whose density is known and stored in the read only memory, or may be an optional liquid, whose density is also known and stored in the ready only memory, or may even be a liquid whose density $D_{OPT}$ had been previously calculated and stored in the random access memory as described heretofore. Regardless of the type of liquid 312 which is used, the container with the liquid therein is placed on the pan, whereupon the apparatus displays the weight $W_L$ of the liquid and container on the display means. Thereafter, the "Tare" key is depressed to store the weight $W_L$ in the random access memory and to "tare" the apparatus and display the net weight. This action involves the subtraction of the combined weight of the liquid and container from itself to provide a "net" signal to the display. Thus, the display means displays the "net" weight, i.e., "0".

The taring of the apparatus readies it for calculating the density of the solid body 310. To that end, in Step 4 the unknown body 310 is immersed in the liquid 312 until the liquid level is at the submersion mark 308 on the suspension wire 306 holding the body. Since the apparatus had heretofore been tared, the submersion of the unknown body within the liquid on the apparatus platform results in the reading on the display of the buoyancy force $W_B$ produced by the displaced liquid. In Step 5, the "Density" and "2" keys are then depressed so that either the standard density $D_{STD}$ or the optional density $D_{OPT}$ are recalled from memory, depending on whether an optional liquid density was previously stored, and to recall from the read only memory the volume $V_{SM}$ of the submerged portion of the suspension means. In Step 6, the density of the body 310 is calculated using the weight of the liquid displaced by the unknown body 310 and the volume of the unknown body 304. To that end, first the volume $V_S$ of the unknown body is calculated by dividing the weight of the liquid displaced (the buoyancy force) $W_B$ just measured by the density $D_L$ of the reference liquid used, i.e., $D_{STD}$ or $D_{OPT}$, and thereafter subtracting the volume $V_{SM}$ of the submerged portion of the suspension means. The volume $V_S$ of the unknown body 310 is displayed by the display means and is now available for use calculating the density of the unknown solid, if desired. To that end, upon depression of the "Density" and "2" keys, the weight $W_S$ of unknown body 310, which is recalled from the random access memory, is automatically divided by volume $V_S$ just calculated to determine the density of the unknown body, which density is displayed by the display means.

The details of the mechanical components and the electrical systems making up the apparatus 20 will be described in detail hereinafter.

Figures 2, 4:
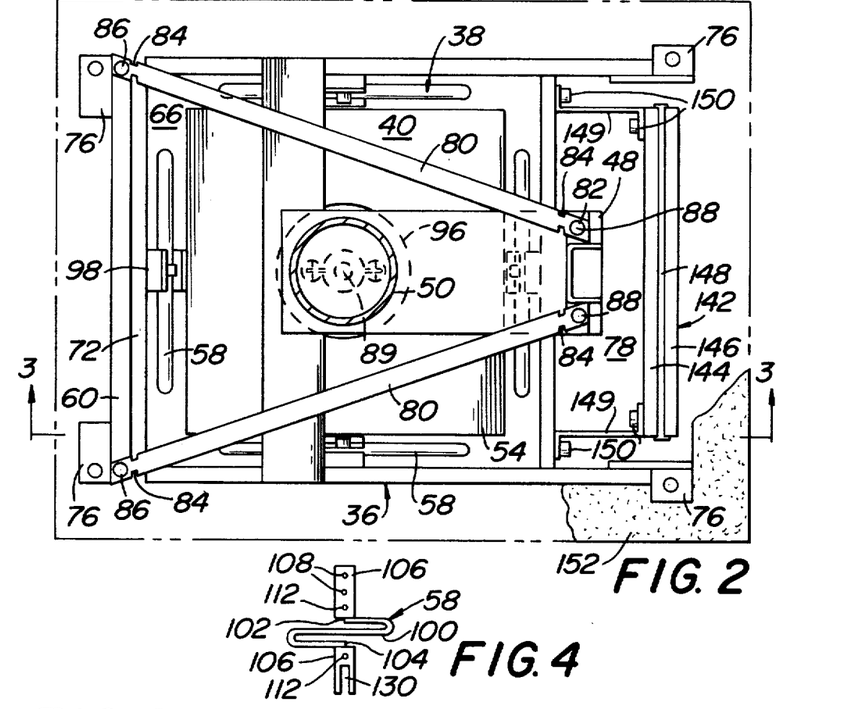
FIG. 2 is a top elevational view of the apparatus shown in FIG. 1 with the casing and platform removed.
FIG. 4 is an elevational view of one of the spring means shown in FIGS. 2 and 3.
Figure 3:
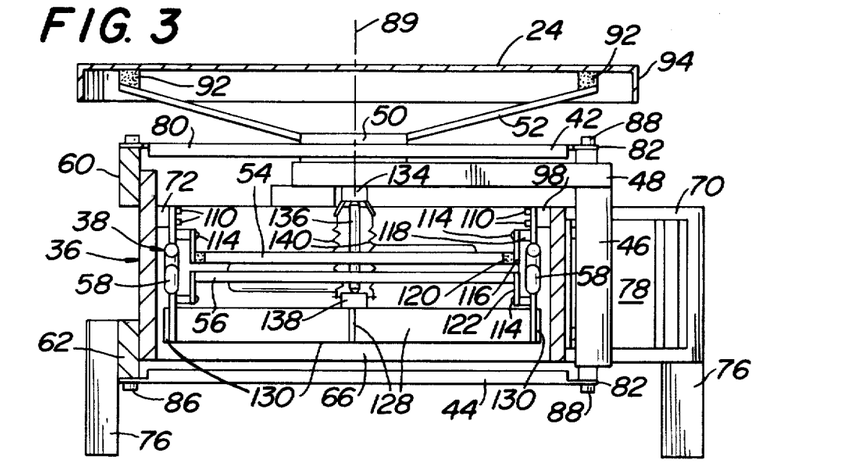
FIG. 3 is a section view taken along line 3—3 of FIG. 2 but showing the platform.

With regard to the mechanical components of the apparatus, attention is directed to FIGS. 2, 3 and 4. As can be seen therein, the apparatus 20 basically comprises a frame assembly 36 supporting various mechanical and electrical components within the casing, a suspension system 38 mounted on the frame assembly and supporting the platform or pan 34 and displacement responsive transducer means 40 coupled to the suspension system and the pan.

The details of the frame and suspension means will be described later, suffice for now to state that the suspension system 38 basically comprises upper and lower parallelogram members 42, and 44, respectively, and an interconnected vertical column 46. An arm 48 extends horizontally from the top of the column 46 just below the upper parallelogram 42. A tubular column 50 is mounted on the arm and terminates at its upper end in a spider 52, upon which the pan 24 is mounted.

The transducer means 40 will be described in detail later, but basically comprises a variable capacitor including an upper plate 54 and a lower plate 56. The lower plate is arranged to be displaced either upward or downward with respect to the upper plate when the pan is similarly displaced by the disposition or removal of a body or material on the pan. The upper plate is fixedly mounted on the frame assembly 36, while the lower plate is suspended from the frame assembly by plural spring members 58. The lower plate 56 is coupled to the pan 24, via the arm 48 and other elements of the suspension system, to be described later.

The use of parallelogram members in a scale suspension system is a conventional technique to insure that only the vertical component of the load is transferred to the pan's displacement detecting means. In the case of this invention, the parallelogram members 42 and 44 and associated components of the suspension system perform that same function. Therefore, only the vertical component of the load on the pan is transferred to the lower capacitor plate 56 by the suspension system. Moreover, the suspension system counteracts all side loads and twisting moments (which might be applied to the pan) and rigidly resists all motions except up/down movement.

The plates 54 and 56 of the capacitor 40 are connected, via electrical conductors (not shown), to the input of a variable frequency oscillator, which will be described in detail later. The oscillator produces an electrical signal, whose output frequency is a function of the capacitance of the capacitor 40, and hence, a function of the vertical displacement of the apparatus pan 24. The electrical signal from the variable frequency oscillator is acted upon by the electronic circuitry of the apparatus 20 to provide a reading of either the weight, volume, or density of the material placed on the pan.

Referring now to FIGS. 2 and 3, the details of the suspension system, the frame assembly, the capacitor and the mounting means therefor will be described in detail. As can be seen from the top view of FIG. 2, the frame is of generally A-shape and is made up of plural bar-like frame elements, specifically a pair of side frame elements 70, an end frame element 72, and an intermediate cross frame element 74. A top bar element 60 is secured to the end frame element 72 at its outer surface contiguous with its upper edge. A similar bar 62 is secured to the outer surface of the cross frame element 72 contiguous with its lower edge. The foregoing frame elements are in turn mounted and supported on plural vertically extending leg elements 76. To that end, a respective leg element 76 is attached to the forward end of each of the side frame elements 70. A pair of leg elements 76 are also connected to the bottom bar 62 at the ends thereof.

The capacitor 40 and its associated mounting and suspension components are located within the space 66 enclosed by the opposed side frame elements 70, the end frame element 72 and the cross frame element 74. The space outside the cross frame element 74, but between the side frame elements 70, and denoted by the reference numeral 78, defines a space in which the interconnecting column 46 is located. In addition, a fixed, or reference capacitor, to be described in detail later, is also mounted on the frame assembly within space 78.

The upper parallelogram member 42 comprises a pair of elongated legs 80, each of which is of U-shaped cross section, except for its opposed end portions 82, each of which is planar. A pair of notches 84 are located in the opposed edges of the planar portions 82 to serve as flex points for the legs of the parallelogram. As can be seen clearly in FIG. 3, the legs of the top parallelogram are mounted by screws 86 on the top bar 60 of the frame assembly. The legs extend at an acute angle to each other, (see FIG. 2), with the free ends of the legs being located in space 78. The lower parallelogram is constructed in an identical manner to the upper parallelogram and also includes a pair of legs 80 which are mounted on the lower bar 62, via screws 86. The free end portions 82 of the legs of the lower parallelogram also terminate within space 78 and directly below the free ends of the upper parallelogram legs.

The interconnecting colunn 46 is an elongated member of U-shaped or tubular cross section and is mounted between the opposed free ends of the two parallelogram members, via respective threaded fasteners 88. The arm 48 is secured to the top of the interconnecting column 46 and, as noted heretofore, extends parallel to the parallelogram legs. The free end of the arm 46 is located approximately centrally with respect to the space 66. The tubular column 50 is mounted on the free end of the interconnecting arm 46, with the longitudinal axis of the column, denoted by the broken line 89, defining the center line for the apparatus pan 24.

The spider 52 includes four angularly extending arms 90, each of which terminates at its free end in a vibration damping cushion 92. The pan 24 is a generally planar member of rectangular shape and having a downwardly projecting flanged peripheral edge 94. The pan is arranged to be disposed on the vibration damping cushions 92 of the spider for support thereon.

As will be appreciated from the foregoing, when a body or material is placed on the pan, irrespective of its position on the pan, only the vertical component of the load is applied to the free end of the arm 46 along axis 88.

The details of the suspension assembly for the capacitor 40 will now be described. The upper plate 54 of the capacitor 40, like the lower plate 56 is a generally planar metallic member, of rectangular shape. Each plate includes a central opening 96 (FIG. 2). The upper plate 54 is fixedly mounted on the frame at the midportion of each of its side edges. The lower plate 56 is mounted on the springs 58 at the midportion of each of its side edges.

The means for mounting the capacitor plate 54 on the frame comprises a mounting block 98 fixedly secured to the inside surface of the side frame elements 70, the end frame element 72 and cross frame element 74, respectively. The mounting blocks 98 each include two openings (not shown) for receipt of respective fastening means to mount a spring 58 and the capacitor plate 54 thereon.

One of the identical springs 58 is shown in FIG. 4 and comprises a generally S-shaped resilient section 100 having an axially aligned opposed pair of ends 102 and 104. A mounting ear 106 is fixedly secured, such as by welding, to the end 102, while a similar ear 106 is secured to the end 104. The upper ears of the springs support the upper plate of the capacitor while the lower ears support the lower plate of the capacitor. Since the ears are secured to axially aligned ends 102 and 104 of the "S-shaped" spring element 100 the displacement of the ears with respect to each other is confined to the axis connecting them, i.e., the vertical axis.

The upper ears 106 are each flat members having three openings therein. The upper of the two openings, designated by the reference numeral 108, serve as the means for mounting the spring 58 on an associated block 98, via threaded fasteners or screws 110. The lower opening 112 of the upper ear is threaded and serves as the means for supporting the fixed capacitor plate 54. To that end, a threaded fastener or screw 114 extends into the opening 112 of the upper ear 106 and an aligned opening (not shown) in an associated hanger strip 116. Each hanger strip is a thin flexible strap-like element. A standoff sleeve 118 is interposed between the strap and the ear to ensure that the strap does not interfere with its associated spring. The lower end of each strap is fixedly secured to the side edge of the upper capacitor plate 58 along an associated side of the plate at the midpoint thereof. A temperature-compensated dielectric material 120 pad is fixedly secured between the hanger strap 116 and side edge of the capacitor plate.

The lower or movable plate 56 of the capacitor 40 is suspended by the four springs 58. To that end, each side edge of the lower plate is supported, via a respective strap 122, on an associated lower ear 106 of an associated spring 58. Each strap 122 is similar in construction to the straps 116 and is fixedly secured at its upper end to the edge of the lower plate 56. The lower end of each strap 122 is secured to the lower ear 106 of an associated spring 58, via a threaded fastener 124 extending through an opening (not shown) in the strap 126 and into an aligned threaded opening 112 in the lower ear 106. A respective standoff sleeve 126 is also interposed between each strap 122 and its associate lower ear 106 to ensure that the strap does not interfere with the associated spring.

A very light weight cross member 128 is also suspended from the springs 58. The member 128 is formed of a pair of thin bars which intersect at their midpoint at right angles. The member 128 is mounted on the lower ear 106 of each spring, via a respective elongated vertical slot 130. To that end, each end of a bar is disposed within an associated slot 130 and welded in place.

The cross member 128 serves to distribute the load, which is applied along axis 89, from the pan 24 to the bottom ear of each of the four springs 58. The springs do not twist as they are stretched or contracted since their S-shape insures that the ends of the spring maintain alignment along the axis of displacement. This action is of significant importance since twisting of the springs would cause hysteresis. It is an important design consideration of the instant invention that the suspension and all of its load-bearing components do not exhibit hysteresis. Moreover friction between the moving components is kept to an absolute minimum.

As should be appreciated from the foregoing description of the suspension system, the capacitor plates 54 and 56 "piggyback" on the springs 58. By "piggyback", it is meant that the plates are attached at points intermediate between the load attachment points on the spring. This construction insures that if displacement occurs at the load application points as the joints are stressed, each spring is displaced as a unit and the upper and lower capacitor plates displace equally, with no relative displacement therebetween.

In order to minimize thermal expansion and friction of the suspension system, the straps 116 and 122 are flexible. The flexiblility of the straps accommodates the thermal expansion of the plates 54 and 56 and slight distortions of the springs, without significant stretch, slippage at the joints, and friction. However, since the straps are rigid in the vertical direction, the plates are firmly fixed in place.

The vertical displacement of the pan 24 along axis 89 is coupled to the lower capacitor plate, via a pushrod bearing assembly to the center of the cross member 128, and from there to the bottom ear of each of the four springs 58. The pushrod bearing assembly comprises a hardened bearing 134 having a central opening (not shown) coaxial with axis 89. An elongated pin or pushrod 136 is mounted between the bearing 134 and a similar bearing 138 mounted on plate 128 coaxial with axis 89. The pushrod 136 extends along axis 89 through the aligned circular openings 96 in the upper and lower capacitor plates 54 and 56, respectively. A pair of tension springs 140 are secured between the bearings 134 and 138 to insure that the pushrod 136 is held in place and that the capacitor plate 56 and the cross member 128 follow the pan during an upward displacement.

As will be appreciated from the foregoing, the load on the pan 24 produced by any body placed thereon is centered along axis 89 and is coupled, via the column arm 48, the upper bearing 134, the pushrod 136 and the lower bearing 138, to the center of the cross member 128, from where it is transferred to the bottom ears 106 of the associated springs. This action causes the uniform stretching of all of the springs. Since the lower plate 56 is mounted on the bottom ear the springs, the lower plate 56 is uniformly displaced downward with respect to the upper plate 54, thereby changing the capacitance of the capacitor 40. Upward displacement occurs in a similar manner.

Because of thermal expansion and the temperature dependence of Young's Modulus, the distance between the plates of capacitor 40 is affected by temperature. Also, the dielectric constant of the air between the plates is a function of the humidity and content of other gases in the air. In order to compensate for the effects of changes in the dielectric constant of the air between the capacitor plates caused by humidity and content of other gases in the air, and changes in Young's Modulus and displacements caused by changes in temperature, the apparatus 20 includes means to compensate for temperature variations and means to compensate for variations in the dielectric constant of the ambient air. To that end, to compensate for variations in the dielectric constant of the ambient air, the apparatus 20 includes a reference capacitor 142 comprising a pair of plates 144 and 146 which are spaced from each other by a fixed air gap 148. Although there may be slight changes in the width of the fixed air gap due to temperature variations, such changes are compensated for in a system algorithm. The fixed capacitor 142 is mounted by a pair of brackets 149 and associated screws 150 onto the intermediate cross frame element 74 in the area 78. The fixed capacitor 142 is connected by conductors (not shown) to a second variable frequency oscillator, to be described in detail later, in the electrical circuitry of the apparatus 20.

Figure 7:
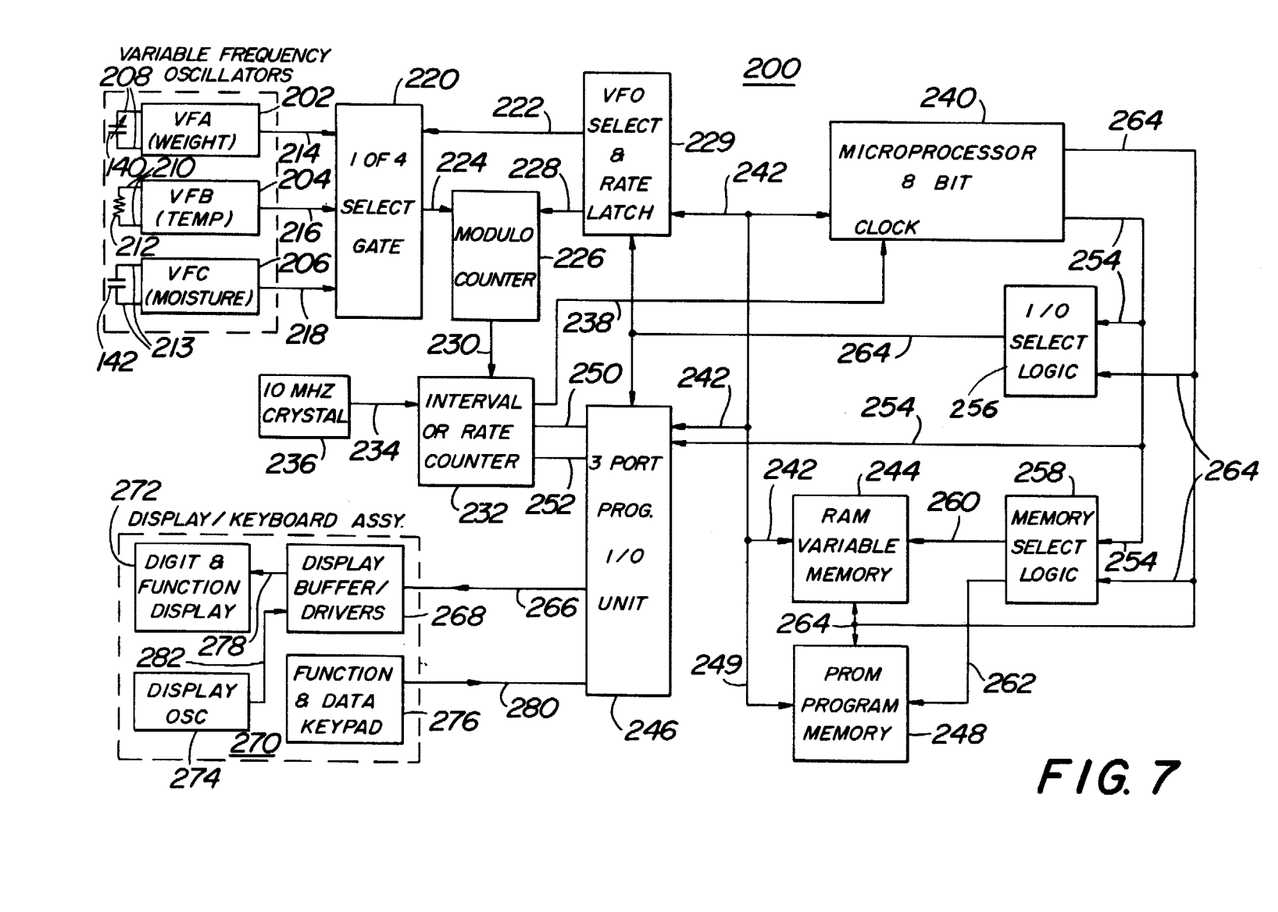
FIG. 7 is a block diagram showing the electrical components of the apparatus forming the instant invention.

To compensate for temperature variations, the apparatus 20 includes a thermistor, shown schematically in FIG. 7, mounted on a portion of the frame within the housing. The thermistor is connected by electrical conductors (not shown) to a third variable frequency oscillator, to be described in detail later, in the electrical circuitry of the apparatus.

The electrical components of the apparatus 20 include, among other things, solid state memory or storage means and microprocessor means including an algorithm complement for effecting the various calculations and routines required of the instant invention. To that end, such storage means include algorithms which compensate for capacitance variations resulting from a change in the dielectric constant of the ambient air and for capacitance variations resulting from thermal expansion/contraction and changes in elastic modulus caused by temperature changes.

In order to insulate the mechanical and electrical components forming the instant invention from changes in the ambient atmosphere, and thereby minimize differences in temperature between the components forming the apparatus 20, an insulated foam box 152, which at a minimum forms dead air spaces between it and the casing, is interposed between the apparatus casing and the frame means 36. Alternatively, a box, air-tight, except for the opening for the pan support column 50, may be used in lieu of the foam box.

The electrical components for the apparatus 20 are shown in block diagram form in FIG. 7. As can be seen therein, the electrical system 200 comprises three variable frequency oscillators 202, 204 and 206. The input to oscillator 202 is provided via a pair of conductors 208. One conductor 208 is connected to the fixed plate 54 of the variable capacitor 40, while the other conductor 208 is connected to the movable plate 56. The variable frequency oscillator 204 includes two input conductors 210 connected to opposite sides of a thermistor 212. The thermistor 212 serves as the means for effecting temperature compensation, as described heretofore. The variable frequency oscillator 206 includes two input conductors 213, one of which is connected to plate 146 of the fixed or reference capacitor 142 and the other is connected to the plate 144.

The output of variable frequency oscillator 202 is connected to a line 214. The output of oscillator 204 is connected to a line 216. The output of oscillator 206 is connected to a line 218. The lines 214, 216 and 218 are connected to three respective inputs of a "1 of 4 Select Gate" 220. The other input to the select gate 220 is connected to line 222. The output of the select gate 220 is connected to line 224, which serves as one input to a "Modulo Counter" 226. Another input to the modulo counter is provided by line 228. The line 228 forms one output of a "VFO Select and Rate Latch" 229. The line 222 serves as another output of the latch 229. The output of modulo counter 226 is connected to line 230, which serves as one input to an "Interval or Rate Counter" 232. Another input to the rate counter is connected to line 234. Line 234 is connected to the output of a 10 megahertz crystal oscillator 236. The rate counter includes one output which is connected to line 238. Line 238 is connected to the clock input of an 8-bit microprocessor 240. The microprocessor 240 is connected to the select latch 229, via a bidirectional data bus 242. The bidirectional data bus 242 is also connected to a "RAM Variable Memory" 244 and to one input of a "Three Port Programmable Input/Output Unit" 246. A "PROM Programmable Memory" 248 is connected, via one way bus 249, to the data bus 242 so that the bus 249 serves as a data input to the PROM. A pair of buses 250 and 252 are connected between the rate counter 232 and the programmable input/output unit 246.

The address output of the microprocessor 240 is connected to an address bus 254. The address bus 254 is connected as one input to an "Input/Output Select Logic Circuit" 256, to one input of a "Memory Select Logic Circuit" 258 and to the address input of the programmable input/output unit 248. One output of the memory select logic is connected, via line 260, to the RAM variable memory 244. Another output of the memory select logic 258 is connected, via line 262, to the PROM 248. The control bus output of the microprocessor 240 is connected to control bus 264. The control bus 264 is connected to another input of the input/output select logic circuit 256, to another input of the memory select logic 258 and to other inputs of the RAM 244 and the PROM 248. The output of the input/output select logic 246 is connected, via bus 264, to one input of the rate latch 229 and to one input of the programmable input/output unit 246. One output of the three-port programmable input/output unit is connected to a display data output bus 266.

The data display output bus is connected to a "Display Buffer/Driver Circuit" 268 in a "Display/Keyboard Assembly" 270. The assembly 270 also comprises a "Digit and Function Display" 272, a "Display Oscillator" 274 and a "Function and Data Keypad" 276. The keypad 276 is connected to the programmable input/output unit 246, via input line 280. The plural keys 32 on the front panel of the case are a portion of the keypad 276, while the digit and function display 272 forms the heretofore identified display means 28. The buffer/driver 268 is connected to the display 272, via bus 278. The oscillator 274 is connected, via line 282, to the display buffer/driver 268.

Operation of the circuitry 200 is as follows: Under the control of the microprocessor 240, the VFO Select and Rate Latch 229 provides appropriate signals, via line 222, to the select gate 220, thereby enabling the gate to pass signals from either the oscillator 202, the oscillator 204 or the oscillator 206. In this regard, the select gate 220 is sequenced periodically by the VFO select 229 under the control of the microprocessor to enable gate 220 to pass signals from the three oscillators 202, 204 and 206 to the modulo counter. The sequencing of the passage of signals from oscillator 202 through gate 220 is preferably arranged to occur anywhere from a few times per second to once every few seconds, while the signals from oscillators 204 and 206 are sequentially passed through gate 220 anywhere from a few times per minute to once every few minutes.

The oscillator 202 is arranged to provide an output signal on line 214 whose frequency is a function of the capacitance of capacitor 40. Since the capacitance of capacitor 40 is a function of the displacement of its plates with respect to each other, and hence the mass of material on the pan, the output frequency appearing on line 214 is a function of the mass of the material on the pan. The signal from oscillator 202 thus passes, via line 224, to the Modulo Counter 226. The modulo counter serves as a ranging device for the input signal. To that end, the Modulo Counter is arranged to provide the input frequency appearing on line 224 by multiplying that frequency by the quantity n/16, where n equals any integer from 1 to 16. The divided output from the counter 226 is provided, via line 230, to the Interval or Rate Counter 232. The Interval or Rate Counter also receives a 10 megahertz reference signal, via line 234, from the crystal oscillator.

The signal from the variable frequency oscillator 204, which is a function of temperature as detected by thermistor 212, is provided, via line 216 and the select gate 220, to the Modulo Counter 226 when the VFO Select and Rate Latch 229 provides an appropriate "select" signal on bus 222. In a similar manner, the oscillator 206 provides a signal, which is a function of the capacitance of the fixed capacitor 142, via line 218, through the select gate 220 and line 224 to the counter 226 when the VFO Select and Rate Latch circuit provides an appropriate "select" signal on line 222.

The Select and Rate Latch also provides the signal for establishing the "n" of the modulo counter 226 along line 228 under the control of the microprocessor 240.

The 10 megahertz signal appearing on line 234 serves as a time base reference for the rate counter 232. The output of the rate counter is a signal which is representative of the number of master clock pulses in a predetermined number of cycles of the frequency of the output signal appearing on line 230 from the modulo counter. The raw data relating to the rate counted is provided, via buses 250 and 252, to the programmable input/output unit 246. Depending upon the address signal received from the microprocessor 240, the input/output unit 246 provides the digitized signals from the interval or rate counter through the bidirectional data bus 242 to the microprocessor 240.

The program in the processor operates on the data input and then provides it into the RAM memory 244 for later processing. The program stored in the microprocessor 240 and in the PROM memory consists of, among other things, the algorithm complement for the system. In particular, the operating program for the system is stored in the PROM and consists of various algorithms including constants to be identified later. The data corresponding to the rate count is operated on in the microprocessor in accordance with the algorithms (and various constants) stored in the PROM 248.

The algorithms for the system 200 are quite long, thus the system 200 is arranged to provide interim calculations before the final calculations. The RAM 244 stores interim calculations.

The input/output select logic gate 256, and the memory select logic gate 258 are conventional devices which are used to control which memory 244 or 246 is being selected by the processor and for controlling the input/output unit 246 and the VFO Select and Rate Latch 229. The operation of the circuit 256, the circuit 258 and the input/output unit 248 is under the control of the control bus signals appearing on bus 264 and the address bus signal line 254 from the microprocessor 240. The control bus signals determine whether the microprocessor is to "read" a particular memory location or to "write" information into a memory location, and hence includes "read", "write" and "address select enable" signals. The address location signals are provided, via line 254, from the microprocessor to the circuit 256, the circuit 258 and the programmable input/output unit 246.

The output signals from the input/output unit 246, which are provided via bus 266, pass to the display 272, whereupon the weight, density, volume, etc., reading of the apparatus 20 is displayed.

The following table represents the components suitable for a commercial embodiment of the invention:

| REFERENCE NUMBER | COMPONENT | PART IDENTIFICATION NO. AND MANUFACTURER |
|---|---|---|
| 202 | Variable Frequency Oscillator | LM331 AN, National Semiconductor |
| 204 | Variable Frequency Oscillator | LM331 AN, National Semiconductor |
| 206 | Variable Frequency Oscillator | LM331 AN, National Semiconductor |
| 220 | One-Of-Four Select Gate | 74LS138, Texas Instruments |
| 226 | Modulo Counter | CD4089, National Semiconductor |
| 229 | VFO Select Gate And Rate Latch | 74C151, National Semiconductor |
| 230 | Rate Counter | 7226B, Intersil |
| 236 | 10 MHZ Crystal | MP-100, CTS Knights |
| 240 | Microprocessor | Z80, Zilog |
| 244 | Random Access Memory | 2114L, Intel |
| 246 | 3 Port Programmable Input/Output Unit | 8255A Intel |
| 248 | Programmable Read Only Memory | 2716, Intel |
| 256 | Input/Output Select | 74LS138, Texas Instruments |
| 258 | Memory Select | 74LS138, Texas Instruments |
| 268 | Display Buffer/Drivers | MD4330BE, Mitel |
| 274 | Display Oscillator | CD4018BC, National Semiconductor |

The algorithm complements stored in the PROM 248 and other parts of the circuitry 200 consists of the following algorithms:

$$T = K_1 - K_2 \ln(N_T - K_3) \tag{1}$$

$$N'_H = N_H - K_4(T - K_5) \tag{2}$$

$$Z_H = [1 - K_6(N'_H/K_7)] \tag{3}$$

$$N'_W = N_W Z_H \tag{4}$$

$$N'_{WO} = N_{WO} Z_H \tag{5}$$

$$Z_T = [1 - K_8(T + K_{10})/K_9] \tag{6}$$

$$W = K_{11}K_{12}Z_T\{K_{13}[(K_{14} - N'_W)/(N'_W - K_{15}) - \tag{7}$$

$$(K_{14} - N'_{WO})/(N'_{WO} - K_{15})] + K_{16}[N'_{WO} - N'_W] +$$

$$K_{17}[(K_{14} - N'_W)/N'_W - (K_{14} - N'_{WO})/N'_{WO}]\}$$

Where $N_H$ is the count from oscillator 206, $N_T$ is the count from oscillator 204 and $N_W$ is the count from oscillator 202 with a body on the pan and $N_{WO}$ is the count from oscillator 202 with nothing on the pan.

Algorithm (1) establishes temperature measurement, algorithm (2) establishes the count based on atmosphere conditions and adjusted for temperature, algorithm (3) establishes the atmospheric conditions factor, algorithms (4) and (5) establish the weight counts adjusted for atmospheric conditions, algorithm (6) establishes the temperature factor and algorithm (7) the weight measurement.

The following constants have been found to be viable for use in the algorithms:

$K_1 = 292.1$ $K_2 = -17.04$ $K_3 = 670,000$ $K_4 = 1174$ $K_5 = 25$ $K_6 = 1.4$ $K_7 = 4,351,947$ $K_8 = 0.05$ $K_9 = 298$ $K_{10} = 273$ $K_{11}$ = depends on attitude/inclination and is "1" when axis 89 is vertical $K_{12}$ = depends on unit of measurement and is "1" when measured in pounds $K_{13} = -3.2$ $K_{14} = 4,381,250$ $K_{15} = -10^6$ $K_{16} = 3.14(10)^{-8}$ $K_{17} = 3.45$ As will be appreciated from the foregoing, the scale of the instant invention provides weight, density or volume readings of great accuracy and precision and which are unaffected by temperature or ambient atmospheric condition changes. The electronic circuitry of the device with its microprocessor and associated control and memory means enables the device to calculate the density of a liquid or the density or volume of a solid directly upon the following of a prescribed routine and without necessitating any manual calculations.

Without further elaboration, the foregoing will so fully illustrate my invention that others may, by applying current or future knowledge, readily adapt the same for use under various conditions of service.

What is claimed as the invention is:

1. Scientific apparatus for automatically determining either the weight, volume or density of an unknown solid or liquid material comprising a housing including scale means having a housing including a platform for receipt of said unknown material thereon and for measuring the weight of said material, computing means, display means, variable capacitance means coupled to said platform and to said computing means and means for compensating for variations in said variable capacitance means caused by temperature variations or changes in the dielectric of said capacitance means caused by changes in the ambient atmosphere, said computing means including memory means, calculating means and control means, said memory means being coupled to the calculating means and the control means for automatically calculating the density of said material, whereupon said display means displays said calculated density.

2. The apparatus of claim 1 for determining the density of an unknown liquid using a standard body, said memory having stored therein the volume of said standard body wherein said computing means, in response to said control means, subtracts the weight of the liquid on the platform from itself, whereupon when said standard body is immersed in said unknown liquid, said computing means determines the weight of the unknown liquid displaced by said body and divides the weight of said displaced liquid by said standard volume to provide a signal indicative of the density of said liquid, which signal is provided to said display means to display said density.

3. The apparatus of claim 1 for determining the density of an unknown solid using a liquid whose density is determined and stored in said memory means, wherein the weight of said solid is measured by said scale means and stored in said memory means and wherein said computing means, in response to said control means, subtracts the weight of the liquid on the plateform from itself, whereupon when said solid is immersed in said liquid said computing means determines the volume of the liquid displaced by detecting the weight of the liquid displaced by said solid and dividing the density of said liquid into said weight, whereafter said computing means divides the weight of said solid by said computed volume to provide a signal indicative of the density of said solid, said signal being provided to said display means to display said density.

4. The apparatus of claim 3 wherein the density of said liquid is determined by said computing means, acting in response to said control means, subtracting the weight of the liquid on the platform from itself, whereupon the standard body is immersed in said unknown liquid, the volume of said standard body being stored in said memory means, said computer means determining the weight of the unknown liquid displaced by said body and thereafter dividing the weight of said displaced liquid by said standard volume to provide a signal indicative of the density of said liquid to said memory means.

5. The apparatus of claim 1 for determining the density of an unknown solid using a liquid whose density is determined and stored in said memory, wherein the weight of said solid is determined by said computing means and stored in said memory means, whereupon when said solid is immersed in said liquid said computing means determines the volume of the liquid displaced thereby by determining the weight of the liquid displaced by said solid and dividing the density of said liquid into said weight, whereafter said computing means divides the weight of said solid by said computed volume to provide a signal indicative of the density of said solid, said signal being provided to said display means to display said density.

6. The apparatus of claim 5 wherein said liquid is disposed on said platform and wherein said computing means, in response to said control means, subtracts the weight of the liquid on the plateform from itself and wherein said solid is thereafter immersed in said liquid on said platform to enable said computing means to determine the volume of the liquid displaced by determining the weight of the liquid displaced by the solid and dividing the density of said liquid into said weight.

7. The apparatus of claim 1 wherein said variable capacitance means is coupled to variable frequency oscillator means and wherein said computing means includes modulo counter means, rate counter means, a fixed frequency oscillator means and wherein said memory means comprises random access memory means and read-only memory means.

8. The apparatus of claim 7 wherein said temperature compensation means comprises thermistor means coupled to variable frequency oscillator means and wherein said dielectric constant compensation means comprises fixed capacitor means coupled to variable frequency oscillator means.

9. An electronic scale comprising: platform means arranged to move upon receipt of some material thereon, support means for said platform means, variable capacitance means coupled to said platform means for providing a first electrical signal indicative of the amount of movement of said platform, fixed capacitance means for providing a second electrical signal dependent upon dielectric changes caused by the ambient atmosphere, temperature responsive means for providing a third electrical signal dependent upon ambient temperature and means for receiving said first, second and third signals for providing a fourth signal indicative of the weight of said material.

10. The scale of claim 9 wherein said scale includes frame means and wherein said support means includes resilient means coupled to said frame means and said platform means and wherein said variable capacitance means comprises a first plate coupled to and arranged for movement with said platform means and a second plate stationarily mounted on said frame means.

11. The scale of claim 10 wherein said resilient means comprises plural springs, each of which is arranged to deflect axially without twisting.

12. The scale of claim 11 wherein said support means comprises a parallelogram suspension assembly.

13. The scale of claim 12 wherein said fixed capacitance means comprises a pair of plates fixedly secured to each other.

14. The scale of claim 13 wherein said temperature responsive means comprises means whose resistance value changes with temperature.

15. The scale of claim 14 including display means for displaying the weight of said material.

16. The scale of claim 15 wherein said scale includes means for storing data therein and for operating upon said first, second, third and fourth signals for taring said scale and for calculating the density of said material and displaying said density on said display means.

17. The scale of claim 16 wherein said scale comprises first, second and third oscillator means coupled to said fixed capacitance means, variable capacitance means and temperature responsive means, respectively, reference oscillator means, counter means, memory means and microprocessor means.

* * * * *